United States Patent [19]

Yang et al.

[11] Patent Number: 4,983,597

[45] Date of Patent: Jan. 8, 1991

[54] BETA-LACTAMS AS ANTICHOLESTEROLEMIC AGENTS

[75] Inventors: Shu S. Yang, Bridgewater; Yuan-Ching P. Chiang, Piscataway; James V. Heck, Scotch Plains, all of N.J.; Michael N. Chang, Newtown, Pa.

[73] Assignee: Merck & Co., Inc., Rahway, N.J.

[21] Appl. No.: 401,391

[22] Filed: Aug. 31, 1989

[51] Int. Cl.$^5$ .................. A61K 31/395; C07D 401/12; C07D 205/08; C07D 403/12

[52] U.S. Cl. .................................... 514/210; 540/200; 540/355

[58] Field of Search .................. 540/355; 514/210

[56] References Cited

U.S. PATENT DOCUMENTS 4,680,391 7/1987 Firestone et al. .................. 540/335
4,778,883 10/1988 Yoshioka et al. .................. 540/200
4,806,564 2/1989 Chabala et al. .................. 514/449
4,816,477 3/1989 Girotra et al. .................. 514/449
4,847,271 7/1989 Chabala et al. .................. 514/336

FOREIGN PATENT DOCUMENTS 63-83062 4/1988 Japan .................. 540/355

Primary Examiner—Mark L. Berch
Attorney, Agent, or Firm—Melvin Winokur; Joseph F. DiPrima

[57] ABSTRACT

Compounds of formula (I), which are useful as antihypercholesterolemic agents, are disclosed.

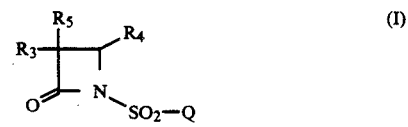

19 Claims, No Drawings

BETA-LACTAMS AS ANTICHOLESTEROLEMIC AGENTS

BACKGROUND OF THE INVENTION

Hypercholesterolemia is known to be one of the prime risk factors for ischemic cardiovascular disease, such as arteriosclerosis. Bile acid sequestrants have been used to treat this condition; but they seem to be moderately effective but they must be consumed in large quantities, i.e., several grams at a time, and they are not very palatable.

MEVACOR ® (lovastatin), now commercially available is one of a group of very active antihypercholesterolemic agents that function by limiting cholesterol biosynthesis by inhibiting the enzyme, HMG-CoA reductase. Another approach to limiting cholesterol biosynthesis is through inhibition of the enzyme HMG-CoA synthase.

Copending U.S. patent application Ser. No. 053,774, filed May 26, 1987 discloses certain $\beta$-lactones of formula (i)

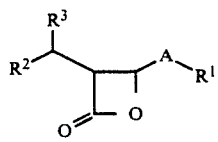

which are useful as antihypercholesterolemic agents and are believed to function by inhibiting HMG-CoA synthase. Additional $\beta$-lactones which have antihypercholesterolemic activity are disclosed in copending U.S. patent applications Ser. No. 021,848, filed Mar. 4, 1987 and Ser. No. 053,646, filed May 26, 1987.

DETAILED DESCRIPTION OF THE INVENTION

The present invention is directed to compounds of structural formula (I):

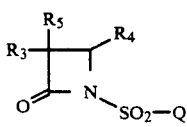

wherein:
Q is
  a. $C_{1-5}$ alkyl,
  b. $C_{6-10}$ aryl or $C_{6-10}$ heteroaryl including one heteroatom selected from N, O, or S;
  c. $C_{7-15}$ aralkyl or $C_{7-15}$ heteroaralkyl;
  d. $C_{6-10}$ aryl or $C_{6-10}$ heteroaryl substituted with W;
  e. $C_{7-15}$ aryl or $C_{7-15}$ heteroaryl wherein the aryl or heteroaryl moiety is substituted with W;
  f. OH;
$R_3 R_5$ are independently selected from:
  a. H,
  b. $C_{1-5}$ hydroxyalkyl,
  c. $C_{1-5}$ alkyl,
  d. $C_{1-5}$ alkoxy,
  e. $C_{2-6}$ alkenyl,
$R_4$ is $CHR_oR$;
$R_o$ is H, $C_{1-5}$ alkyl, phenyl or phenyl $C_{1-5}$ alkyl;
R is
  a. $O-(CO)_{p2}-(A)_{p1}-R_1$,
  b. $OSO_2R_1$,
  c. $AR_1$,
  d. R together with $R_o$ and the C to which it is attached form

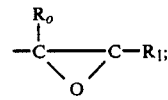

e. R together with $R_o$ and the C to which it is attached form

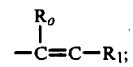

$p_1$ and $p_2$ are independently 0 or 1; provided that p, and $p_2$ are not both 0;
$R_1$ is
  a. H,
  b. aryl, or a heteroaryl group of 5 to 10 atoms, including one to two heteroatoms, selected from:

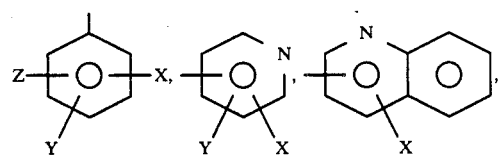

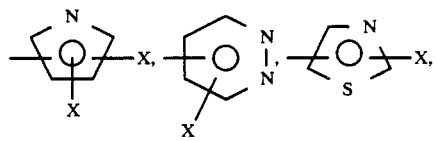

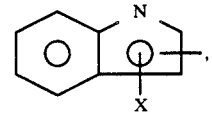

c. phenyl $S(O)_n$ wherein n is 0 to 2,
  d. $C_{3-6}$ cycloalkyl;
M is O, N or S;
A is
  a.

b.

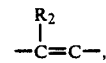

c. NH;
$R_2$ is
  a. H,
  b $C_{1-5}$ alkoxy,
  c. Chd 1-5 alkyl,
  d. OH,
  e. $OC(O)CH_3$;
W is
  a. $C_{1-5}$ alkyl, b. $C_{1-5}$ alkoxy,
c. $NO_2$,
d. $NHR_3$,
e. $C_{1-3}$ alkylS(O)$p_3$
   $p_3$ is 0 to 2,
f. halogen,
g. $COOR_3$,
h. $OCOR_3$,
i. $NHCOR_3$,
j. $NHSO_2R_3$,
k. $NHSO_2$phenyl;

X, Y, and Z are independently selected from:

a. H,
b. halogen,
c. Chd 1-5 alkyl
d. $C_{1-5}$ alkoxy,
e. $C_{1-5}$ alkoxycarbonyl
f. $C_{1-5}$ alkylcarbonyloxyamino,
g. amino,
h. phenoxy,
i. phenyl $C_{1-5}$ alkoxy,
j. $C_{1-5}$ alkylSO$_2$NH,
k. $NO_2$,
l. diphenylmethyloxycarbonyl,
m. $C_{1-5}$ alkylthio,
n. aminocarbonyl,
o. carboxy,
P $C_{1-5}$alkenyloxy
q. $C_{1-5}$alkylamido,
r. trifluoromethyl.

One embodiment of the present invention are those compounds of formula (I) wherein:

R is $O(CO)p_2$-(A)$p_1$-$R_1$ or $OSO_2R_1$, and $R_o$ and $R_5$ are H.

In one class of this embodiment are those compounds wherein R is $O$-$(CO)p_2$-$(A)p_1$-$R_1$.

In One subclass are those compounds wherein $P_1$ is 0 and $P_2$ is 1 and Q is 4-methylphenyl or OH. Exemplifying this subclass are the compounds of formula (I) described in Table I.

TABLE I

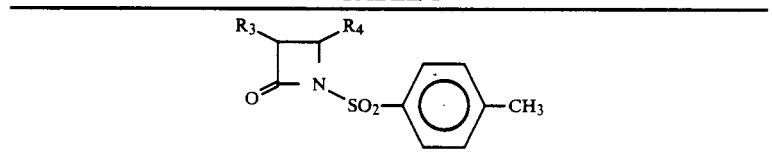

| | | | CONFIGURATION AT 3,4 POSITIONS | | |
|---|---|---|---|---|---|
| | | $R_3$ | $R_4$ | | $IC_{50}$ |
| a. | cis | $CH_3CH_2$— | 3-thienyl$CO_2CH_2$— | | $7.1 \times 10^{-7}$ |
| b. | cis | $CH_3CH_2$— | 3-methanesulfonamidophenyl-$CO_2CH_2$— | | $2.5 \times 10^{-8}$ |
| c. | cis | $CH_3CH_2$— | 2-nitrophenyl$CO_2CH_2$— | | $2.3 \times 10^{-8}$ |
| d. | cis | $CH_3CH_2$— | 4-pyridyl$CO_2CH_2$— | | $6.2 \times 10^{-8}$ |
| e. | cis | $CH_3CH_2$— | 2-pyridyl$CO_2CH_2$— | | $5.4 \times 10^{-8}$ |
| f. | cis | $CH_3CH_2$— | 5-(2-methoxypyridyl)$CO_2CH_2$— | | $4.1 \times 10^{-8}$ |
| g. | cis | $CH_3CH_2$— | 2-furanyl$CO_2CH_2$— | | $7.9 \times 10^{-9}$ |
| h. | cis | $CH_3CH_2$— | 2-(5-n-butylpyridyl)$CO_2CH_2$— | | $4.5 \times 10^{-8}$ |
| i. | 3S,4S | $CH_3CH_2$— | 4-methoxyphenyl$CO_2CH_2$— | | $3.0 \times 10^{-8}$ |
| j. | 3R,4R | $CH_3CH_2$— | 4-methoxyphenyl$CO_2CH_2$— | | $2.0 \times 10^{-7}$ |
| k. | cis | $CH_3CH_2$— | 3-nitrophenyl$CO_2CH_2$— | | $3.9 \times 10^{-8}$ |
| l. | cis | $CH_3CH_2$— | 2-$CH_3SO_2$NHphenyl$CO_2CH_2$— | | $3.1 \times 10^{-8}$ |
| m. | cis | $CH_3CH_2$— | 4-pyridazinyl$CO_2CH_2$— | | $8.2 \times 10^{-8}$ |
| n. | cis | $CH_3CH_2$— | 2-$NH_2$phenyl$CO_2CH_2$— | | $3.1 \times 10^{-8}$ |
| o. | cis | $CH_3CH_2$— | 3-furanyl$CO_2CH_2$— | | $3.2 \times 10^{-7}$ |
| p. | cis | $CH_3CH_2$— | 2-quinolinyl$CO_2CH_2$— | | $2.1 \times 10^{-8}$ |
| q. | cis | $CH_3CH_2$— | 4-benzyloxyphenyl$CO_2CH_2$— | | $4.0 \times 10^{-8}$ |
| r. | cis | $CH_3CH_2$— | 4-quinolinyl$CO_2CH_2$— | | $2.5 \times 10^{-8}$ |
| s. | cis | $CH_3CH_2$— | 2-thienyl$CO_2CH_2$— | | $3.8 \times 10^{-8}$ |
| t. | cis | $CH_3CH_2$— | 3-(2-phenoxypyridyl)$CO_2CH_2$— | | $3.3 \times 10^{-8}$ |
| u. | cis | $CH_3CH_2$— | 3-$CH_3$CONHphenyl$CO_2CH_2$— | | $7.2 \times 10^{-8}$ |
| v. | cis | $CH_3CH_2$— | 3-$NH_2$phenyl$CO_2CH_2$— | | $4.5 \times 10^{-8}$ |
| w. | cis | $CH_3CH_2$— | 4-((Ph)$_2$COOC)phenyl$CO_2CH_2$— | | $6.2 \times 10^{-8}$ |
| x. | cis | $CH_3CH_2$— | 4-HOOCphenyl$CO_2CH_2$— | | $3.5 \times 10^{-7}$ |
| y. | cis | $CH_3CH_2$— | 4-$NO_2$phenyl$CO_2CH_2$— | | $2.8 \times 10^{-8}$ |
| z. | cis | $CH_3CH_2CH_2$— | 4-$CH_3$Ophenyl$CO_2CH_2$— | | $6.95 \times 10^{-8}$ |
| aa. | cis | $HOCH_2$— | 4-$CH_3$Ophenyl$CO_2CH_2$— | | $1.8 \times 10^{-7}$ |
| bb. | cis | $CH_3CH_2$— | 3-pyridyl$CO_2CH_2$— | | $6.4 \times 10^{-8}$ |
| cc. | cis | $CH_3CH_2$— | 4-$CH_3$Ophenyl$CO_2CH_2$— | | $3.0 \times 10^{-8}$ |
| dd. | cis | $CH_3CH_2$— | phenyl$CO_2CH_2$— | | $1.1 \times 10^{-7}$ |
| ee. | cis | $CH_3CH_2$— | 3-Coumaryl$CO_2CH_2$— | | $5.0 \times 10^{-8}$ |
| ff. | cis | $CH_3CH_2$— | 2-benzofuranyl$CO_2CH_2$— | | $3.3 \times 10^{-8}$ |
| gg. | S,S | $CH_3CH_2$— | 2-furanyl$CO_2CH_2$— | | $1.1 \times 10^{-8}$ |
| hh. | cis | $CH_3CHCH_3$— | 4-methoxyphenyl$CO_2CH_2$— | | $1.3 \times 10^{-7}$ |
| ii. | cis | $CH_3CH_2$— | 4-$CH_3O_2$Cphenyl$CO_2CH_2$— | | $8.5 \times 10^{-9}$ |
| jj. | cis | $CH_3CH_2$— | 4-n-butylcarbamoylphenyl$CO_2CH_2$— | | $2.0 \times 10^{-8}$ |
| kk. | cis | $CH_3CH_2$— | 4-aminophenyl$CO_2CH_2$— | | $4.7 \times 10^{-8}$ |
| ll. | cis | $CH_3CH_2$— | 3-methoxy-4-allyloxy-5-nitro-phenyl$CO_2CH_2$— | | $1.6 \times 10^{-7}$ |
| mm. | cis | $CH_3CH_2$— | 3-methoxy-4-allyloxy-5-(methylamido)phenyl$CO_2CH_2$— | | $3.0 \times 10^{-7}$ |
| nn. | cis | $CH_3CH_2$— | 4-methanesulfonamidophenyl$CO_2CH_2$— | | $1.6 \times 10^{-8}$ |
| oo. | cis | $CH_3CH_2$— | 5-(2,3-dimethoxypyridyl)$CO_2CH_2$— | | $3.8 \times 10^{-8}$ |
| pp. | cis | $CH_3CH_2$— | 6-(2,3-dimethoxypyridyl)$CO_2CH_2$— | | $8.9 \times 10^{-8}$ |
| qq. | cis | $CH_3CH_2$— | 4-(2-methoxythiazoly)$CO_2CH_2$— | | $4.5 \times 10^{-8}$ |

TABLE I-continued

![structure with R3, R4, N-SO2-phenyl-CH3]

| | CONFIGURATION AT 3,4 POSITIONS | $R_3$ | $R_4$ | $IC_{50}$ |
|---|---|---|---|---|
| rr. | trans | $CH_3CH_2CH_2-$ | $4-CH_3OphenylCO_2CH_2-$ | $3.5 \times 10^{-8}$ |
| ss. | trans | $HOCH_2-$ | $4-CH_3OphenylCO_2CH_2-$ | $1.5 \times 10^{-7}$ |
| tt. | trans | $CH_3CH_2-$ | $4-CH_3OphenylCO_2CH_2-$ | $1.7 \times 10^{-7}$ |

In a second subclass are those compounds of formula (I) wherein $p_1$ is 1 and $_2$ is 1. Exemplifying this subclass are the compounds of formula (I) described in Table II.

TABLE II

![structure with R3, R4, N-SO2-phenyl-CH3]

| | CONFIGURATION AT 3, 4 POSITIONS | $R_3$ | $R_4$ | $IC_{50}$ |
|---|---|---|---|---|
| a. | cis | $CH_3CH_2-$ | $4-CH_3OphenylC=CCO_2CH_2-$ | $9.5 \times 10^{-9}$ |
| b. | cis | $CH_3CH_2-$ | $4-CH_3OphenylCH_2CO_2CH_2-$ | $3.5 \times 10^{-8}$ |
| c. | cis | $CH_3CH_2-$ | $3-pyridylCH_2CO_2CH_2-$ | $3.5 \times 10^{-8}$ |
| d. | 3S,4S | $CH_3CH_2-$ | phenyl-(R)—$CHOCH_3CO_2CH_2-$ | $1.8 \times 10^{-8}$ |
| e. | 4S | H | phenyl-(S)—$CHOCH_3CO_2CH_2-$ | $4.2 \times 10^{-8}$ |
| f. | 4S | H | phenyl-(R)—$CHOCH_3CO_2CH_2-$ | $5.0 \times 10^{-8}$ |
| g. | cis | $CH_3CH_2-$ | phenyl-(R)—$CHOCH_3CO_2CH_2-$ | $6.7 \times 10^{-8}$ |
| h. | cis | $CH_3CH_2-$ | $3-pyridylC=CCO_2CH_2-$ | $3.1 \times 10^{-8}$ |
| i. | 3S,4S | $CH_3CH_2-$ | $3-pyridylCH_2CO_2CH_2-$ | $8.7 \times 10^{-9}$ |
| j. | 3S,4S | $CH_3CH_2-$ | $4-methoxyphenylCH_2CO_2CH_2-$ | $8.6 \times 10^{-9}$ |
| k. | 3S,4S | $CH_3CH_2-$ | $4-methoxyphenylC=CCO_2CH_2-$ | $1.1 \times 10^{-8}$ |
| l. | cis | $CH_3CH_2-$ | $2-furanylCH_2CO_2CH_2-$ | $2.4 \times 10^{-6}$ |
| m. | cis | $CH_3CH_2-$ | $2-furanylC=CCO_2CH_2-$ | $2.5 \times 10^{-7}$ |
| n. | cis | $CH_3CH_2-$ | $phenoxyCH_2CO_2CH_2-$ | $2.4 \times 10^{-8}$ |
| o. | cis | $CH_3CH_2-$ | $3-methyl-4-ethoxyphenylCH_2CO_2CH_2-$ | $2.1 \times 10^{-9}$ |
| p. | cis | $CH_3CH_2-$ | $2-pyridylCH_2CO_2CH_2-$ | $1 \times 10^{-8}$ |
| q. | cis | $CH_3CH_2-$ | $phenylthioCH_2CO_2CH_2-$ | $4.2 \times 10^{-8}$ |
| r. | cis | $CH_3CH_2-$ | $4-ethoxyphenylCH_2CO_2CH_2-$ | $2.2 \times 10^{-8}$ |
| s. | cis | $CH_3CH_2-$ | $3,4,5-trimethoxyphenylCH_2CO_2CH_2-$ | $2.0 \times 10^{-8}$ |
| t. | cis | $CH_3CH_2-$ | $3.4,5-trimethoxyphenylC=CCO_2CH_2-$ | $3.8 \times 10^{-8}$ |
| u. | cis | $CH_3CH_2-$ | 3-bromo-4-propanoxy-5-methoyxy-phenylC=CCO_2CH_2- | $9 \times 10^{-8}$ |
| v. | cis | $CH_3CH_2-$ | $4-methylphenylaminoCO_2CH_2-$ | $5.2 \times 10^{-8}$ |
| w. | cis | $CH_3CH_2-$ | $cyclohexylaminoCO_2CH_2-$ | $5.4 \times 10^{-8}$ |
| x. | cis | $CH_3CH_2-$ | 4-triflurormethylphenylamino-$CO_2CH_2-$ | $2.6 \times 10^{-7}$ |
| y. | cis | $CH_3CH_2-$ | $3,4-dimethoxyphenylCH_2CO_2CH_2-$ | $3 \times 10^{-8}$ |
| z. | cis | $CH_3CH_2-$ | $6-(2,3-dimethoxypyridyl)C=CCO_2CH_2-$ | $2.7 \times 10^{-8}$ |
| aa. | cis | $CH_3CH_2-$ | $4-fluorophenylaminoCO_2CH_2-$ | $5.0 \times 10^{-8}$ |

Double bonds within the $R_4$ moiety are in the trans configurations.

In a second class of this embodiment are those compounds wherein R is $OSO_2R_1$. Exemplifying this class is the compound described in Table III.

TABLE III

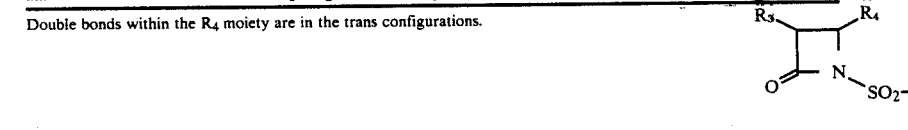

| | CONFIGURATION AT 3, 4 POSITIONS | | |
|---|---|---|---|
| | $R_3$ | $R_4$ | $IC_{50}$ |
| cis | $CH_3CH_2-$ | $4-CH_3phenylSO_2OCH_2-$ | $1.1 \times 10^{-7}$ |

In a second embodiment of the present invention are those compounds of formula (I) wherein:
R is $O-(CO)p_2-(A)p_1-R_1$, $AR_1$ R together with $R_o$ and the C to which it is attached form

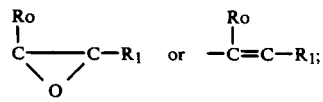

$P_1$ and $P_2$ are independently 1 to 1, provided that $P_1$ and $P_2$ are not both zero;

$R_o$ is H, CH$_3$, or phenyl; provided that when R is O-(CO)$_{p2}$(A)$_{p1}$-R$_1$, R$_o$ is CH$_3$ or phenyl;

$R_5$ is H.

In one class of this embodiment are the compounds wherein:

R is

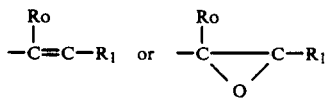

$R_o$ is H, or CH$_3$. Exemplifying this class are the compounds in Table IV.

TABLE IV

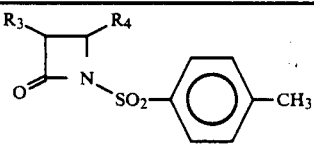

| | CONFIGURATION AT 3,4 POSITIONS | | |
|---|---|---|---|
| | $R_3$ | $R_4$ | IC$_{50}$ |
| a. | trans | CH$_3$CH$_2$CH$_2$— | phenylC≡C— | 1.5 × 10$^{-6}$ |
| b. | cis | CH$_3$CH$_2$CH$_2$— | phenylC≡C— | 2.2 × 10$^{-6}$ |
| c. | trans | HOCH$_2$— | phenylC≡C— | 1.1 × 10$^{-6}$ |
| d. | cis | HOCH$_2$ | phenylC≡C— | 1.1 × 10$^{-6}$ |
| e. | trans | CH$_3$CH$_2$— | phenylC≡CCH$_3$ | 5.0 × 10$^{-5}$ |
| f. | cis | CH$_3$CH$_2$— | phenylC≡CCH$_3$ | 4.3 × 10$^{-7}$ |

In a second class are the compounds wherein:

R is O-(CO)$_{p2}$-(A)$_{p1}$-R$_1$ or AR$_1$;

$R_0$ is H, CH$_3$ or phenyl; provided that when R is O-(CO)$_{p2}$-(A)$_{p1}$-R$_1$, $R_o$ is CH$_3$ or phenyl.

Further illustrating this class are those compounds wherein P$_1$ is 0. Exemplifying this class are the compounds of table V.

TABLE V

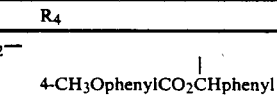

| | CONFIGURATION AT 3, 4 POSITIONS | | |
|---|---|---|---|
| | $R_3$ | $R_4$ | IC$_{50}$ |
| a. | cis CH$_3$CH$_2$— | 4-HO$_2$CphenylNHCH$_2$— | 9.9 × 10$^{-6}$ |
| b. | cis CH$_3$CH$_2$— | phenylCH$_2$CH$_2$— | 8.6 × 10$^{-8}$ |
| c. | cis CH$_3$CH$_2$— | 4-CH$_3$OphenylCO$_2$CHCH$_3$ (with vertical bar) | 1.2 × 10$^{-7}$ |
| d. | cis CH$_3$CH$_2$— | phenylCH$_2$CHCH$_3$ (with vertical bar) | 1.75 × 10$^{-7}$ |

TABLE V-continued

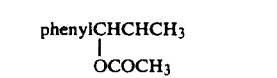

| | CONFIGURATION AT 3, 4 POSITIONS | | |
|---|---|---|---|
| | $R_3$ | $R_4$ | IC$_{50}$ |
| e. | cis CH$_3$CH$_2$— | 4-CH$_3$OphenylCO$_2$CHphenyl (with vertical bar) | 2 × 10$^{-6}$ |
| f. | H | phenylCHCHCH$_3$ / OCOCH$_3$ | 4.9 × 10$^{-7}$ |
| g. | H | CH$_3$CO$_2$CH$_2$CHCH$_3$ | 2.9 × 10$^{-7}$ |

A third embodiment of the present invention is presented by those compounds of formula (I) wherein:

$R_o$ is H, CH$_3$ or CH$_2$phenyl;

$R_5$ is C$_{1-5}$ alkyl, or C$_{1-5}$ alkoxy; and

R is O-(CO)$_{P2}$-(A)$_{P1}$-R$_1$, AR$_1$, or R together with R$_o$ and the C to which it is attached form

P$_1$ and P$_2$ are independently 0 or 1; provided that both P$_1$ and P$_2$ are not both zero. Exemplifying this embodiment are those compounds of formula (I) described in Table VI.

TABLE VI

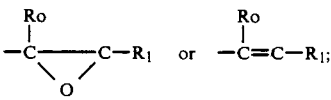

| | $R_3$ | $R_5$ | $R_4$ | IC$_{50}$ |
|---|---|---|---|---|
| a. | CH$_3$ | CH$_3$ | phenylCH$_2$CH$_2$— | 1.8 × 10$^{-6}$ |
| b. | CH$_3$ | CH$_3$ | phenylCO$_2$CHCH$_2$phenyl | 4 × 10$^{-7}$ |
| c. | CH$_3$ | CH$_3$ | phenylCH=CH— | 6.8 × 10$^{-7}$ |
| d. | CH$_3$ | CH$_3$ | phenylCH——CH—/O | 1.1 × 10$^{-7}$ |

The alkyl groups referred to above may be straight chain or branched or may include cycloalkyl groups. Halogen or halo means fluoro, chloro, bromo or iodo.

The non-optically active compounds of the present invention may be prepared according to Scheme I. Trimethylsilyl amine is added to an α, β unsaturated aldehyde to form an amine which is then condensed with an ester moiety for form a β-lactam of formula (I-1). Compound (I-1) may, under ozonolysis conditions, be converted to the aldehyde (I-1) or the alcohol (I-3) or (I-1) may be reduced to compound (I-4) which can be sulfonated at the lactam nitrogen. Compound (I-1) may also be converted to the epoxide which can be converted to esters of formula (I-6). The aldehyde compound (I-2) may be treated with a Grignard reagent to form compounds of formula (I-7) where $R_o$ is methyl or phenyl or benzyl. The alcohol (I-3) can be protected at the hydroxyl group, then sulfonated, deprotected and treated with an acylating agent to form compounds of formula (I-9) or an isocyanate to form compounds of formula (I-10). In the alternative the acylation at the hydroxyl group may precede the sulfonation at the lactam nitrogen.

Substituents on an aryl moiety either in R' or R" can be formed after acylation or sulfonation by conversion of aryl substituents such as $-NO_2$ to $-NH_2$ followed by further conversion of amino to an amide or sulfonamide functionality.

SCHEME I

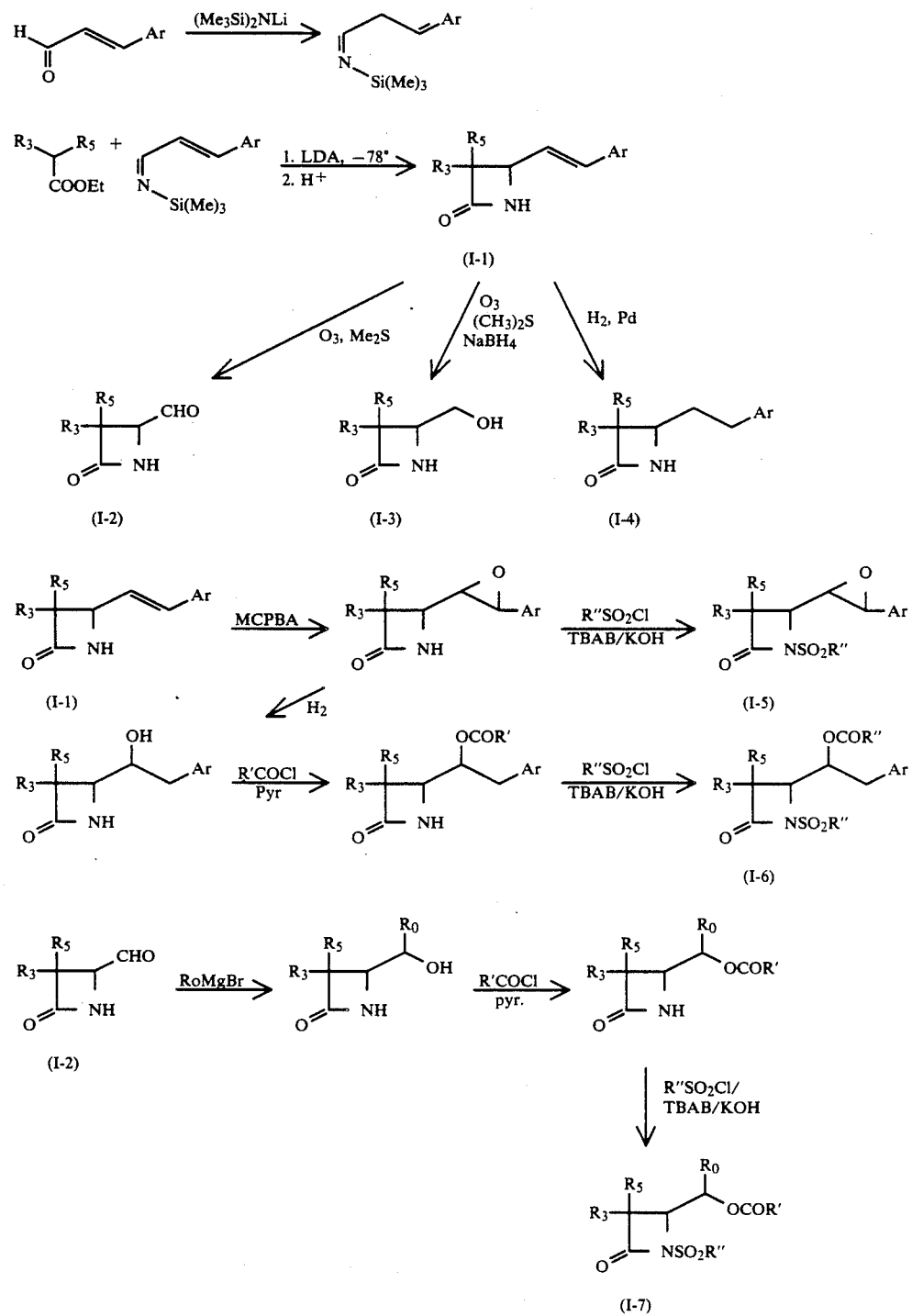

-continued
SCHEME I
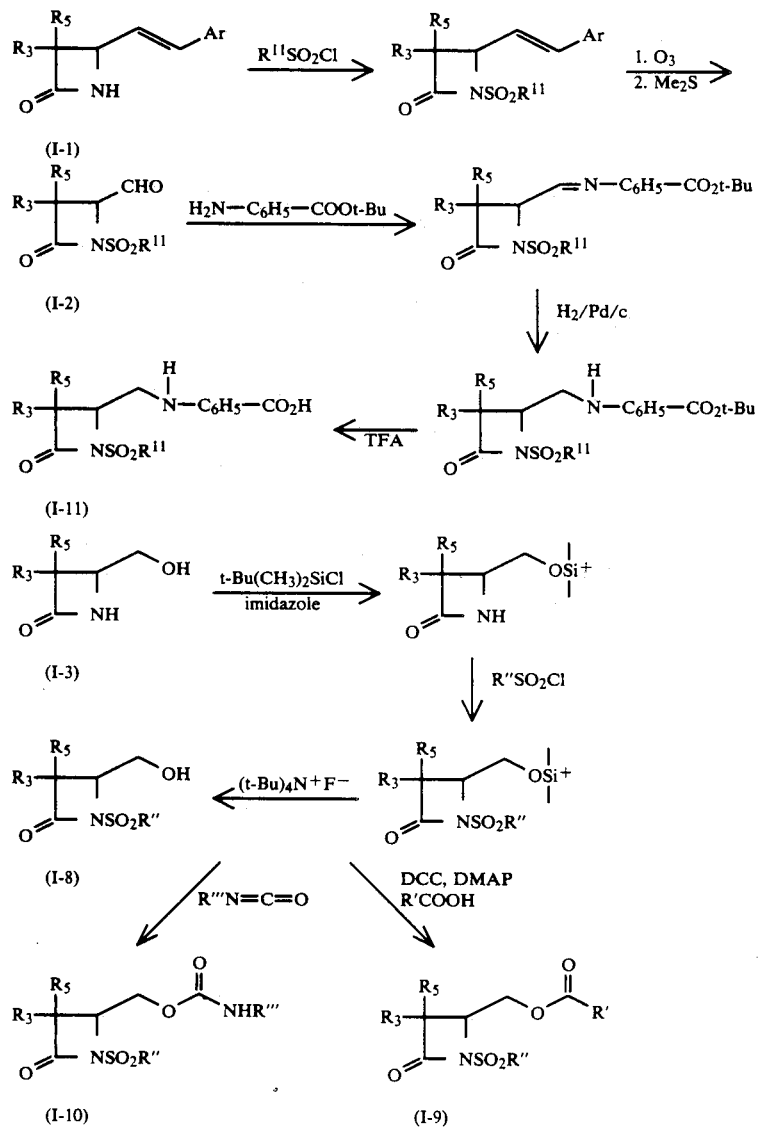
The optically active compounds of the present invention can be prepared as outlined in Scheme II.
SCHEME II
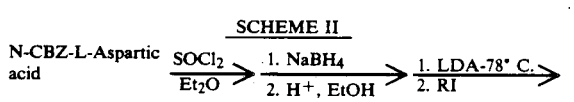
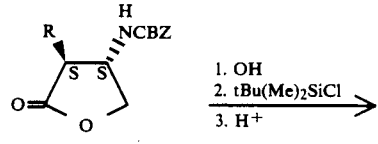
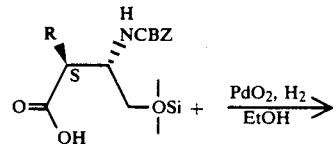
-continued
SCHEME II
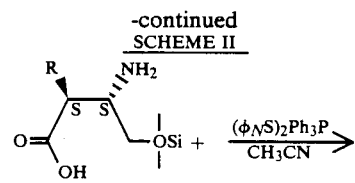
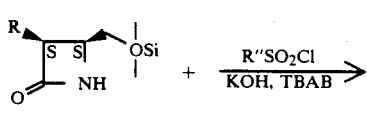
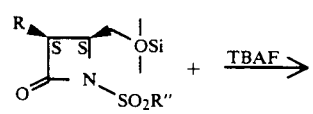

-continued
SCHEME II

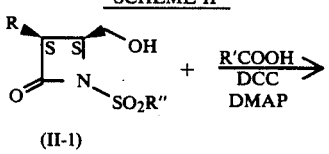

(II-1)

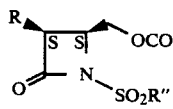

Where the cis R,R stereoisomer is desired it may be formed in the above sequence by employing D-aspartic acid in place of L-aspartic acid. The alcohol (II-1) may be further converted to the corresponding alkyl halide with retention of configuration.

The present invention is also directed to a method of inhibiting cholesterol biosynthesis which comprises the administration to a subject in need of such treatment a nontoxic, therapeutically effective amount of a compound represented by the following general structural formula (I) and pharmaceutically acceptable salts thereof.

The present invention is also directed to a method of inhibiting the activity of HMG-CoA synthase enzyme which comprises the administration to a subject in need of such treatment a nontoxic, therapeutically effective amount of a compound represented by the general structural formula (I) and pharmaceutically acceptable salts thereof.

Specifically the compounds of this invention are useful as antihypercholesterolemic agents for the treatment of arteriosclerosis, hyperlipidemia, familiar hypercholesterolemia and the like diseases in humans. They may be administered parenterally in the form of a capsule, a tablet, an injectable preparation or the like. Doses may be varied, depending on the age, severity, body weight and other conditions of human patients but daily dosage for adults is within a range of from about 20 mg to 2000 mg (preferably 20 to 100 mg) which may be given in two to four divided doses. Higher doses may be favorably employed as required.

The pharmaceutically acceptable salts of the compounds of this invention include those formed from cations such as sodium, potassium, aluminum, calcium, lithium, magnesium, zinc, and from bases such as ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

The compounds of this invention may also be coadministered with pharmaceutically acceptable nontoxic cationic polymers capable of binding bile acids in a non-reabsorbable form in the gastrointestinal tract. Examples of such polymers include choloestyramine, colestipol and poly[methyl-(3-trimethylaminopropyl-)imino-trimethylene dihalide]. The relative amounts of the compounds of this invention and these polymers is between 1:100 and 1:15,000.

The intrinisic HMG-CoA synthase inhibition activity of the compounds of this invention is measured by the standard in vitro protocol described below:

The livers from male Charles River CD rats (225-350 g) were homogenized in 0.25 M sucrose which was adjusted with phenylmethylsulfonylfluoride (PMSF) and N-p-tosyl-1-lysine chloromethyl ketone (TLCK) so that the final concentration of each was 50 and 25 mg/ml, respectively. The homogenate was centrifuged at 15,000× g for 20 minutes, the supernatant filtered through a fine nylon screen to remove most of the fat layer and recentrifuged at 100,000× g for 1 hour. This supernatant was removed and 1 M potassium phosphate, dithiothreitol (DTT) and ethylene glycolbis($\beta$-aminoethyl ether)-N,N,N',N'-tetraacetic acid (EGTA) added to give a final concentration of 0.1 M (pH 7.2), 0.5 mM and 0.1 mM, respectively. Solid ammonium sulfate was added to 50% saturation to the protein solution, it was centrifuged at 15,000× g and the supernatant discarded. This precipitated protein could be stored at −70° C. for at least one month with very little loss of activity. The ammonium sulfate precipitate was dissolved in an minimal amount of 0.06 M potassium phosphate buffer (pH 7.2) containing 0.5 mM dithiothreitol and 0.1 mM EGTA (referred to as 0.06 M phosphate buffer) and dialyzed overnight against 2 liters of the same buffer to remove the ammonium sulfate and to inactivate HMG-CoA lyase [Clinkenbeard, et al., J. Biol. Chem. 250, 3108–3116(1975)].

The dialyzed extract was added to a column of DEAE-52 (Whatman) which had been equilibrated with 0.06 M phosphate buffer (10 mg of protein in 1 ml bed volume of the resin). The DEAE-cellulose was eluted with 0.06 M phosphate buffer until the optical density at 280 nm was essentially zero. This fraction contained the $\beta$-ketoacetyl-CoA thiolase activity. The HMG-CoA synthase was eluted from the column with 0.1 M phosphate buffer (pH 7.2) containing 0.5 mM DTT and 0.1 nM EGTA, and was virtually free of all thiolase activity. The protein was precipitated by the addition of ammonium sulfate to give 50% saturation. This solution was stirred for 10 minutes at 4° C. and the precipitate collected by centrifugation at 15,000 rpm for 10 minutes. The supernatant was discarded and the precipitate dissolved in a minimum of 0.06 M phosphate buffer, pH 7.2 (about 10 ml) and the enzyme stored at −80° C.

HMG-CoA Synthase Inhibition Assay

Enzyme protein (ca. 24 mg) was added to a solution containing 117 $\mu$M Tris-HCl (pH 8.0), 11.7 $\mu$M MgCl$_2$, 1.17 $\mu$M ethylenediaminetetraacetic acid (EDTA), 0.58 $\mu$M dithiothreitol, and the indicated concentrations of the test compound (added as a 2 mg/ml solution in dimethylsulfoxide). The incubation took place in a volume of 0.085 ml at 30° in a shaking water bath. After 5 minutes, 15 ml of a solution containing acetoacetyl-CoA and 0.1 $\mu$Ci of 1-[$^{14}$C]-acetyl-CoA was added to give a final concentrations of 0.1 and 0.4 $\mu$M, respectively. The incubation was continued for 10 more minutes and the reaction stopped by the addition of 50 ml of the assay mixture to 0.2 ml of 6N HCl in a glass scintillation vial. The vial was heated for 1 hour at 120° after which time 0.2 ml more of 6N HCl was again added to each vial and the heating continued for another hour. Following this, 1.0 ml of 0.9% saline was added to each vial and finally 10 ml of scintillation liquid. Radioactivity was determined in a Packard Tri-Carb liquid scintillation counter. Percent inhibition is calculated by the formula:

$$1 - \frac{\text{Sample} - \text{Blank}}{\text{Control} - \text{Blank}}$$

IC$_{50}$ values were determined by plotting the log of the concentration of the test compound verses the percentage inhibition and fitting a straight line to the resulting data by using the least squares method.

The following examples illustrates the preparation of compounds of formula (I) and as such are not to be considered as limiting the invention set forth in the claims appended hereto.

EXAMPLE 1

Preparation of (±)-cis-3-Ethyl-4-hydroxymethyl-2-azetidinone

Method I

Step A: Generation of N-Trimethylsilyl Imine Solution:

To a cooled solution of 10.54 ml (50 mmol) of 1,1,1,3,3,3-hexamethyldisilazane in 36 ml of anhydrous THF at −78° C. was added 19.24 ml (48.1 mmol) of 2.5 M n-butyllithium in hexane in one portion. The resulting solution was stirred for 30 minutes at −78° C. and to this solution was then added dropwise 5.7 ml (45.4 mmol) of cinnamaldehyde in 12 ml of THF. The mixture was stirred for 1½ hours and the resulting cold solution of N-trimethylsilyl imine was used directly in the following reaction.

Step B: Preparation of (±)-cis-3-Ethyl-4-(β-styryl)-2-azetidinone

To a cooled solution of 7.26 ml (51.7 mmol) of diisopropylamine in 40 ml of THF at −78° C. was added 21 ml (52.5 mmol) of 2.5 M n-butyllithium. The solution was stirred for 10 minutes at −78° C. then 15 of 6 ml (45.4 mmol) of ethyl butyrate in 12 ml of THF. After stirring for 1 hour at −78° C., to this solution was added dropwise the above generated (Step 3A) cooled solution of N-trimethylsilyl imine. The resulting mixture was stirred at −78° C. for 1 hour then at room temperature for 2 hours, quenched with 300 ml of cooled 1 N HCl, and extracted with 3×100 ml ether. The ether phases were combined, dried and concentrated. The product was purified by flash column chromatography (R$_f$=0.25, 30% EtOAc in hexane) to afford the product β-lactam.

NMR (CDCl$_3$): δ1.00 (3H, t), 1.48–1.88 (2H, m), 3.32 (1H, m), 4.40 (1H, m), 6.12 (1H, s), 6.24 (1H, dd), 6.64 (1H, d), 7.21–7.38 (5H, m).

Step C: Preparation of (±)-cis-3-Ethyl-4-hydroxymethyl-2-azetidinone

A solution of 13 g (64.5 mmol) of (±)-cis-3-ethyl-4-(β-styryl)-2-azetidinone in 400 ml of CH$_2$Cl$_2$ was ozonized at −78° C. until the solution turned blue. The resulting solution was stirred for 20 minutes at −78° C. then 30 minutes at room temperature. The solution was recooled to −78° C. and to this solution was added 14 ml (190 mmol) of methyl sulfide. After stirring for 10 minutes at −78° C. and 50 minutes at room temperature, the solution was concentrated and the residue was redissolved in 400 ml of methanol and cooled to 0° C. 5.5 g (149 mmol) of sodium borohydride was added slowly to the cooled solution. The resulting mixture was stirred for 20 minutes at 0° C. the ½ hour at room temperature and concentrated. The product was purified by flash column chromatography to yield the titled compound. NMR (CDCl$_3$): δ1.08 (3H, t), 1.50–1.89 (2H, m), 3.17 (1H, m) 3.66–4.00 (3H, m), 6.89 (1H, s).

Method II

To a solution of 500 mg of (±)-cis-3-ethyl-4-benzyloxycarbonyl-2-azetidinone (2.1 mmol) in 20 ml of anhydrous THF was added dropwise 1.0 ml of 2M lithium borohydride-THF solution. The mixture was stirred at room temperature for 5 hours and quenched with 1.5 ml of methanol dropwise in the cold. The mixture was concentrated and the residue purified by preparative tln silica gel plates developed with ethyl acetate to give the titled compound.

EXAMPLE 2

Preparation of (±)-cis-3-Ethyl-4-hydroxymethyl-N-toluenesulfonyl-2-azetidinone Step A: Preparation of (±)-cis-3-Ethyl-4-t-butyldimethylsilyloxymethyl-2-azetidinone 187 mg of (±)-cis-3-ethyl-4-hydroxymethyl-2-azetidinone, 300 mg of imidazole, and 300 mg of t-butyldimethylsilyl chloride in 3 ml dry dimethylformamide (DMF) were stirred at room temperature for 2 hours. The mixture was concentrated to dryness and 25 ml of H$_2$O:EtOAc (2:3) were added. The mixture was washed 3 times with 3 ml of H$_2$O to remove DMF and imidazole and then dried over Na$_2$SO$_4$ and concentrated to yield the titled compound as white crystals. NMR (CDCl$_3$): δ0.06 (6H, s), 0.89 (9H, s), 1.06 (3H, t), 1.48–1.88 (2H, m), 3.14 (1H, m), 3.56–3.90 (3H, m), 5.86 (1H, brs).

Step B: Preparation of (±)-cis-3-Ethyl-4-t-butyldimethylsilyloxymethyl-N-toluenesulfonyl-2-azetidinone The product of Step 2A and 300 mg of tosyl chloride were dissolved in 10 ml of 1% tetrabutylammonium bromide solution (CH$_3$CN:CH$_2$Cl$_2$=1:19). 100 mg KOH was added and the mixture stirred for one hour. The mixture was filtered and the filtrate concentrated to give the crude product.

NMR (CDCl$_3$): δ0.07 (6H, d), 0.88 (9H, s), 1.04 (3H, t), 1.8 (2H, m), 2.44 (3H, s), 3.15 (1H, m), 3.84–4.16 (3H, m), 7.4 (2H, d), 7.9 (2H, d).

Step C: Preparation of (±)-cis-3-Ethyl-4-hydroxymethyl-N-toluenesulfonyl-2-azetidinone To the product of Step 2B (100 mg) dissolved in 2 ml of THF was added 150 μl of aqueous HF, and the mixture stirred at room temperature for 4 hours. The mixture was filtered through silica and washed with 1:1 EtOAc/aq. NaHCO$_3$ and dried over Na$_2$SO$_4$. The mixture was filtered and concentrated to a colorless oil which was flash chromatographed to yield the title compound.

NMR (CDCl$_3$): δ1.04 (3H, t), 1.50–1.92 (2H, m), 2.47 (3H, s), 2.65 (1H, brs), 3.15 (1H, dt), 3.80–4.15 (3H, m), 7.40 (2H, d), 7.90 (2H, d).

EXAMPLE 3

Preparation of
(±)-cis-3-Ethyl-4-p-methoxyphenylacetoxymethyl-N-toluenesulfonyl-2-azetidinone To (±)-cis-3-ethyl-4-hydroxymethyl-N-toluenesulfonyl-2-azetidinone (3.3 mg) and p-methoxyphenylacetic acid (3.7 mg) in $CH_2Cl_2$ (0.6 ml) was added dicyclohexylcarbodiimide (DCC) (5 mg) followed by p-dimethylaminopyridine (DMAP) (1 mg). The mixture was stirred overnight, at room temperature and then purified via preparative tlc on a silica gel plate and developed with $CH_2Cl_2$ to yield the titled compound.

NMR ($CDCl_3$): $\delta 0.94$ (3H, t), 1.22–1.74 (2H, m), 2.44 (3H, s), 3.18 (1H, dt), 3.45 (2H, q), 3.79 (3H, s) 4.20–4.50 (3H, m), 6.98 (4H, dd), 7.61 (4H, dd).

EXAMPLE 4

Preparation of
(±)-cis-3-Ethyl-4-(2-phenyl)ethyl-2-azetidinone

To (±)-cis-3-ethyl-4-($\beta$-styryl)-2-azetidinone (28 mg) in 2 ml of EtOAc was added 3 mg of 10% Pd/C. The mixture was hydrogenated at room temperature and 1 atmosphere. ($H_2$ consumed = 0.000139 moles). The solution was filtered and the filtrate concentrated and purified by preparative tlc, to yield the titled compound.

NMR ($CDCl_3$): $\delta 1.06$ (3H, t), 1.45–2.08 (4H, m) 2.70 (2H, dt), 3.11 (1H, dt) 3.70 (1H, m) 5.70 (1H, brs) 7.10–7.39 (5H, m).

EXAMPLE 5

Preparation of cis-(3S),
(4S)-3-Ethyl-4-[(R)-α-methoxyphenylacetoxyl]methyl-N-toluenesulfonyl-2-azetidinone and cis-(3R),
(4R)-3-Ethyl-4-[(R)-α-methoxyphenylacetoxyl]methyl-N-toluenesulfonyl-2-azetidinone

Step A: Preparation of cis(±)-3-Ethyl-4-[(R)-α-methoxyphenylacetoxy]methyl-2-azetidinone To (±)-cis-3-ethyl-hydroxymethyl-2-azetidinone (26 mg) and R-(−)-α-methoxyphenylacetic acid (54 mg) in $CH_2Cl_2$ (6 ml) was added DCC (62 mg) followed by addition of p-dimethylaminopyridine (12 mg). The mixture was stirred at room temperature overnight and the filtrate concentrated and purified via preparative tlc on a silica gel plate (1500 μ) and developed with $CH_2Cl_2$ halfway and then EtOAc:$CH_2Cl_2$=1:1 to yield the titled compound.

NMR ($CDCl_3$): $\delta 1.00$ and 1.01 (3H, 2t), 1.2–1.8 (2H, m), 3.15 (1H, m), 3.21 (3H, s), 3.79 (1H, m), 4.15 (1H, m), 4.38 (1H, m), 4.80 (1H, s), 5.61 (1H, brs), 7.40 (5H, m).

Step B: Preparation of cis(±)-3-Ethyl-4-[(R)-α-methoxyphenylacetoxy]methyl-N-toluenesulfonyl-2-azetidinone To the product of Step 5A (20 mg) in 0.8 ml of 1% tetrabutyl ammonium bromide solution ($CH_3CN:CH_2Cl_2$, 1:19) (TBAB solution) was added excess tosyl chloride and pulvertized KOH. The mixture was stirred at room temperature for 36 hours. The mixture was then filtered and concentrated and the residue purified by preparative tlc on a silica gel plate (1500 μ) developed halfway with $CH_2Cl_2$ and then 5–10% EtOAc in $CH_2Cl_2$, to yield the title compound.

NMR ($CDCl_3$): $\delta 0.78$ and 0.88 (3H, 2t), 1.00–1.70 (2H, m), 2.45 and 2.47 (3H, 2s), 3.1 (1H, m), 3.38 and 3.42 (3H, 2s), 4.10–4.38 (2H, m), 4.40–4.60 (1H, m), 4.49 and 4.80 (1H, 2s), 7.20–7.97 (9H, m).

Step C: Separation of cis-(3S), (4S)-3-Ethyl-4-[(R)-α-methoxyphenylacetoxy]methyl-N-toluenesulfonyl-2-azetidinone and cis-(3R), (4R)-3-Ethyl-4-[(R)-α-methoxyphenylacetoxy]methyl-N-foluenesulfonyl-2-azetidinone The product of Step 5B (3.6 mg) in $CH_2Cl_2$ (0.25 ml) was spotted dropwise on 2 silica gel plates (250 μ) and developed with:
EtOAc:Hexane=1:9 4 times
EtOAc:Hexane=1:8 2 times
EtOAc:Hexane=1:7.5 once
to give the (3S), (4S) titled compound (high $R_f$); NMR ($CDCl_3$): $\delta 0.88$ (3H, t), 1.14–1.70 (2H, m), 2.45 (3H, s), 3.1 (1H, m), 3.42 (3H, s), 4.12–4.38 (2H, m), 4.48–4.60 (1H, m), 4.80 (1H, s), 7.20–7.90 (9H, m); and the (3R), (4R) titled compound (low $R_f$) NMR ($CDCl_3$): $\delta 0.78$ (3H, t), 1.00–1.78 (2H, m), 2.47 (3H, s), 3.1 (1H, m), 3.38 (3H, s), 4.10–4.38 (2H, m), 4.40–4.60 (1H, m), 4.49 (1H, s), 7.20–7.96 (9H, m).

EXAMPLE 6

Preparation of
cis-(3S),(4S)-3-Ethyl-4-hydroxymethyl-N-toluenesulfonyl-2-azetidinone and
trans-(3R),(4S)-3-Ethyl-4-hydroxymethyl-N-toluenesulfonyl-2-azetidinone

Step A: Preparation of (3S)-3-Benzyloxycarbonylamino-2-ethyl-Ybutyrolactone

The title compound was prepared from N-CBZ-L-aspartic acid in three steps via the formation of N-CBZ-L-aspartic acid anhydride and (3S)-3-benzyloxycarbonylamino-Y-butyrolactone according to the published procedure by Y. Takahashi et al., *Chem. Pharm. Bull.*, 34, 3020 (1986).

Step B: Preparation of (3S)-3-Benzyloxycarbonylamino-4-t-butyldimethyl-silyloxy-2-ethylbutyric acid To a solution of (3S)-3-Benzyloxycarbonylamino-2-ethyl-Y-butyrolactone (24 g) in 300 ml of methanol was slowly added 100 ml of 1 N NaOH at 0° C. The mixture was stirred at 0°–5° C. for 25 minutes and then at room temperature for 20 minutes. Methylene chloride was added (2×150 ml) followed by the addition of 2.5 N HCl to bring the pH of the aqueous layer to 6.0. Ethyl acetate (900 ml) was added to the aqueous solution and the EtOAc layer concentrated to an off-yellow oil. The aqueous layer was brought to pH=3.0 and then extracted again with EtOAc. The two EtOAc extracts were combined and dried over $Na_2SO_4$ and concentrated to a yellow oil which then crystallized in an ice bath.

The crystallized product was combined with 75 g t-butyldimethylsilyl chloride and 70 ml of triethylamine and 400 ml of DMF and stirred for 2 hours. The precipitated salts were filtered and the filtrate stirred for 30 minutes and then concentrated to 100 ml. An ethyl ether:water (1000 ml:200 ml) mixture was added and the ether layer concentrated to a yellow oil which was then dissolved in 500 ml of methanol. The mixture was stirred at 0° C. and 100 ml of 1 N HCl added and stirred for 15 minutes at 0° C. and 10 minutes at room temperature. 80 ml of 1 N NaOH was added to bring the pH to 5.0 and the mixture concentrated to 200 ml. The EtOAc layer was washed with sat. NaCl and dried and concentrated to a brown oil. The crude solid was purified by flash chromatography to yield the titled compound.

NMR (CDCl₃): δ0.07 (6H, s), 0.86 (9H, s), 0.08–1.12 (2H, m), 1.5–1.9 (2H, m) 2.56 (1H, m), 3.68 (1H, m), 3.98 (1H, m) 4.25–4.50 (1H, m), 5.12 (2H, s), 5.26 (1H, d), 7.36 (5H, s).

Step C: Preparation of (3S)-3-Amino-4-t-butyldimethylsilyloxy-2-ethylbutyric Acid To a solution of the product of Step 6B in 500 ml of methanol was added 2.0 grams of 10% Pd/C and the mixture hydrogenated over hydrogen at 40 psi. The catalyst was removed by filtration and the solution concentrated to a colorless oil. The oil crystallized in ether/hexane. The solid was broken up, filtered and washed with ether to yield the titled compound which was employed in the next step.

Step D: Preparation of (4S)-4-t-Butyldimethylsilyloxymethyl-3-ethyl-2-azetidinone The product from Step 6C (8.0 g), 11.0 g of triphenylphosphine, 8.8 g of 2,2'-dipyridyl disulfide in 3 liters of CH₃CN were heated for 4 hours. The mixture was concentrated to dryness, redissolved in CH₂Cl₂ and stirred at 0° C. with the addition of 16 ml of Et₃N 20 ml of CH₃I. The mixture was stirred for 30 minutes at 0° C. and concentrated to dryness. Ether (500 ml) was added and the insoluble salts filtered off. The ether solution was concentrated to a reddish oil and the crude product flash chromatographed using the following solvent gradient:

| 1 l | 30% CH₂Cl₂/hexane |
| 1 l | 50% CH₂Cl₂/hexane |
| 1 l | CH₂Cl₂ |
| 500 ml | ether | to yield the titled product.

NMR (CDCl₃): δ0.06 (6H, s), 0.88 (9H, s), 1.06 (3H, t), 1.50–1.86 (2H, m), 3.14 (1H, m), 3.58–3.86 (3H, m), 5.86 (1H, brs).

Step E: Preparation of (4S)-4-t-Butyldimethylsilyloxymethyl-3-ethyl-N-toluenesulfonyl-2-azetidinone The product of Step 6D (2.0 g), 20 g of tosyl chloride and 1.2 g of powdered KOH were stirred in 120 ml of 5% CH₃CN in CH₂Cl₂ containing 1% tetrabutylammonium bromide, at 0° C. for 15 minutes, then room temperature for 90 minutes. The mixture was chromatographed (CH₂Cl₂:hexane:ether=3:7:1) to yield a 3:1 cis:trans mixture.

NMR (CDCl₃): δ0.07 (6H, s), 0.87 (9H, s) 1.05 (3H, t), 1.58–1.94 (2H, m), 2.45 (3H, s), 3.15 (1H, m), 3.82–4.14 (3H, m), 7.36 (2H, d), 7.88 (2H, d).

Step F: Preparation of cis-(3S),(4S)-3-Ethyl-4-hydroxymethyl-N-toluenensulfonyl-2-azetidinone and trans-(3R),(4S)-3-Ethyl-4-hydroxymethyl-N-toluenesulfonyl-2-azetidinone The mixture from Step 8E was dissolved in 50 ml of THF and 1.0 g of tetrabutylammonium fluoride and 2.0 ml of 50% HF were added. The mixture was stirred at 0° C. for 30 minutes, then room temperature for 18 hours. Saturated NaHCO₃ solution was added to neutralize the reaction mixture followed by ether/H₂O with stirring for 30 minutes. The mixture was filtered, concentrated to dryness and dissolved in ether/EtOAc. The mixture was flash chromatographed to yield the cis (S,S) and trans (R,S) isomers.

NMR of cis isomer (CDCl₃): δ1.04 (3H, t), 1.5–1.9 (2H, m), 2.47 (3H, s), 2.70 (1H, dd(, 3.15 (1H, dt), 3.82–4.12 (3H, m), 7.38 (2H, d), 7.90 (2H, d).

NMR of trans isomer (CDCl₃): δ0.92 (3H, t), 1.32–1.94 (2H, m), 2.46 (3H, s), 2.49 (1H, m), 3.80–4.30 (3H, m), 4.78 (IH, m), 7.36 (2H, d), 7.78 (2H, d).

EXAMPLE 7

Preparation of cis-(3S), (4S)-3-Ethyl-4-m-pyridine acetoxymethyl-N-toluenesulfonyl-2-azetidinone cis-(3S),(4S)-3-Ethyl-4-hydroxymethyl-N-toluenesulfonyl-2-azetidinone (137 mg) and 70 mg of 3-pyridylacetic acid, 125 mg of DCC, and 5 mg of DMAP in 5 ml CH₂Cl₂ were stirred at room temperature for 18 hours. The mixture was worked up and the product crystallized from EtOAc/hexane.

NMR (CDCl₃): δ0.97 (3H, t), 1.3 1.8 (2H, m), 2.44 (3H, s), 3.20 (1H, dt), 3.60 (2H, s), 4.2–4.6 (3H, m), 7.2–7.9 (8H, m).

EXAMPLE 8

Preparation of cis-(3R),(4R)-3-Ethyl-4-hydroxymethyl-N-toluenesulfonyl-2-azetidinone and trans-(3S),(4R)-3-Ethyl-4-hydroxymethyl-N-toluenesulfonyl-2-azetidinone Using N-CBZ-D-aspartic acid in place of N-CBZ-L-aspartic acid and employing the procedure of Example 6 the titled compounds were obtained.

EXAMPLE 9

Preparation of (±) cis-3-Ethyl-4-hydroxycarbonylphenylaminomethyl-N-toluenesulfonyl-2-azetidinone

Step A: Preparation of (±)-cis-3-Ethyl-4-(β-styryl)-N-toluenesulfonyl-2-azetidinone 70 mg of (±)-cis-3-Ethyl-4-(β-styryl)-2-azetidinone was dissolved in 3 ml of TBAB solution; 100 mg of tosyl chloride and 20 mg KOH were added and stirred at 0° C. for 15 minutes, and then room temperature for one hour. The crude product was chromatographed on a silica column using 20% EtOAc in hexanes as eluent to give the titled compound.

NMR (CDCl₃): δ0.96 (3H, t), 1.40–1.86 (2H, m), 2.43 (3H, s), 3.32 (1H, m), 4.76 (1H, m), 5.92 (1H, dd), 6.73 (1H, d), 7.29 (7H, m), 7. 81 (2H, d).

Step B: Preparation of (±)-cis-3-Ethyl-4-formyl-N-toluenesulfonyl-2-azetidinone The product of step (9A) was dissolved in 5 ml of a 2:1 mixture of CH₂Cl₂ and methanol. The mixture was stirred at −78° C. and ozone was bubbled in until a blue color presisted. The mixture was stirred at 78° C. for 30 minutes and then room temperature for 30 minutes. Dimethyl sulfide (200μl ) was added and the mixture stirred at room temperature for 1 hour. TLC showed the absence of starting material. The solution was concentrated to give the crude titled compound without further purification.

Step C: Preparation of Schiff Base

To the mixture of step (9B) was added methanol (0.8 ml) and 20 mg. of t-butyl-p-aminobenzoate and 5 mg toluenesulfonic acid and the mixture stirred at room temperatur for 18 hours, to yield the crude Schiff base.

Step D: Preparation of (±) cis-3-Ethyl-4-t-butoxycarbonylphenylaminomethyl-N-toluenesulfonyl-2-azetidinone The product of step (9C) was hydrogenated at 40 psi in the pressence of 10% Pd/C. Flash chromatography gave the crude titled product.

Step E: Preparation of (±) cis 3-Ethyl-4-hydroxycarbonyl-phenylaminomethyl-N-toluenesulfonyl-2-azetidinone The tert-butyl moiety was cleaved using 30% trifluoroacetic acid (TFA) in CH$_2$Cl$_2$ for 5 hours to give the titled compound.

EXAMPLE 10

Preparation of (±)-3,3-Dimethyl 4-(1,2-epoxy-2-phenyl)ethyl-N-toluenesulfonyl-2-azetidinone

Step A: Preparation of (±)-3,3-Dimethyl-4-(1,2-epoxy-2-phenyl)ethyl-2-azetidinone To 670 mg of (±)-3,3-Dimethyl-4-(β-styryl)-2-azetidinone in 10 ml of CH$_2$Cl$_2$ was added 616 mg of m-chloroperbenzoic acid. The mixture was stirred overnight, and filtered. The filtrate was purified via prep. tlc on silica gel plates developed with CH$_2$Cl$_2$:hexane (1:1). The impure product was further purified via prep. tlc on silica gel plates developed with EtOAc:hexane (2:3) to give the titled compound NMR (CDCl$_3$): δ1.28 (3H, s), 1.40 (3H, s), 3.1 (1H, dd), 3.26 (1H, d), 3.69 (1H, d), 6.17 (1H, brs).

Step B: Preparation of (±)-3,3-Dimethyl-4-(1,2-epoxy-2-phenyl)ethyl-N-toluenesulfonyl-2-azetidinone To 25 mg (±)-3,3-Dimethyl-4-(1,2-epoxy-2-phenyl)ethyl-2-azetidinone in 0.3 ml of TBAB solution was added 120 mg of tosyl chloride and 20 mg of pulverized KOH. The mixture was stirred at room temperature overnight. The mixture was filtered and the filtrate purified via prep. tlc on silica gel (1000μ) developed with hexane:CH$_2$Cl$_2$ (1:4) to give the titled compound.

NMR (CDCl$_3$): δ1.21 (3H, s), 1.25 (3H, s), 2.45 (3H, s), 3.06 (1H, dd), 3.51 (1H, d), 3.82 (1H, d), 7.2–7.5 (7H, m), 7.60 (2H, m).

EXAMPLE 11

Preparation of (±)-3,3-Dimethyl-4-(1-benzoyloxy-2-phenyl)ethyl-N-toluenesulfonyl-2-azetidinone

Step A Preparation of (±)-3,3-Dimethyl-4-(1-hydroxy-2-phenyl)ethyl-2-azetidinone A solution of 64 mg of (±)-3,3-Dimethyl-4-(1,2-epoxy-2-phenyl)ethyl-2-azetidinone in 5 ml of EtOAc was hydrogenated at 1 atm. in the presence of palladium for 1 hour. The mixture was filtered through a celite pad washed with EtOAc/MeOH. The filtrate was concentrated to give the titled compound.

NMR (CDCl$_3$) δ1.28 (3H, s), 1.34 (3H, s) 2.64 (1H, dd), 2.86 (1H, dd), 3.30 (1H, d), 3.87 (1H, t), 6.05 (1H, s), 7.0–7.5 (5H, m).

Step B: Preparation of (±)-3,3-Dimethyl-4-(1-benzoyloxy-2-phenyl)ethyl-2-azetidinone To 25 mg of the product of step (11A) in 0.5 ml of CH$_2$Cl$_2$ was added 0.2 ml of pyridine and then a solution of 0.1 ml of benzoyl chloride in 0.2 ml of CH$_2$Cl$_2$. The mixture was stirred at room temperature for 2 hours and concentrated. The residue was pumped to dryness and purified via prep. tlc on silica gel (1500μ) developed with 10% EtOAc in CH$_2$Cl$_2$ to give the titled compound.

NMR (CDCl$_3$): δ1.24 (3H, s), 1.33 (3H, s), 3.06 (2H, ddd), 3.58 (1H, d), 5.50 (1H, dd), 5.61 (1H, m), 7.1–7.7 (8H, m), 8.0 (2H, dd).

Step C: Preparation of (±)-3,3-Dimethyl-4-(1-benzoyloxy-2-phenyl)ethyl-N-toluenesulfonyl-2-azetidinone To the product of step (11B) in 0.2 ml of TBAB solution was added 50 mg of tosyl chloride and 10 mg of pulverized KOH and the mixture stirred at room temperature overnight. The mixture was purified via prep. tl c on silica gel (1000μ) and developed with CH$_2$Cl$_2$ halfway and then 2% EtOAc in CH$_2$Cl$_2$ to give the titled compound.

NMR (CDCl$_3$): δ3.14 (3H, s), 3.15 (3H, s), 2.40 (3H, s), 3.24 (2H, ddd), 4.03 (1H, d), 5.36 (1H, m), 7.2–7.6 (10H, m), 7.70 (2H, dd), 7.89 (2H, d).

What is claimed is:

1. A compound of structural formula (I)

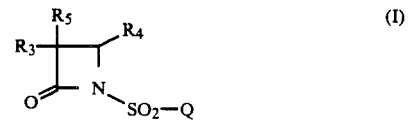

wherein:
Q is
  a. C$_{1-5}$ alkyl,
  b. C$_{6-10}$ aryl or C$_{6-10}$ heteroaryl including one heteroatom selected from N, O, or S;
  c. C$_{7-15}$ aralkyl or C$_{7-15}$ heteroaralkyl;
  d. C$_{6-10}$ aryl or C$_{6-10}$ heteroaryl substituted with W;
  e. C$_{7-15}$ aralkyl or C$_{7-15}$ heteroaryl wherein the aryl or heteroaryl moiety is substituted with W wherein, in Q, the heteroaryl in hetereoaryl or heteroaralkyl consists of the rings given in the R$_1$ detinition, choice (b), except for the first of those rings, in which X, Y and M are given there;
R$_3$ and R$_5$ are independently selected from:
  a. H,
  b. C$_{1-5}$ hydroxyalkyl,
  c. C$_{1-5}$ alkyl,
  d. C$_{1-5}$ alkoxy,
  e. C$_{2-6}$ alkenyl;
R$_4$ is CHR$_o$R;
R$_o$ is H, C$_{1-5}$ alkyl, phenyl or phenyl C$_{1-5}$ alkyl; R is
  a. O-(CO)$_{P2}$-(A)$_{P1}$-R$_1$,
  b. OSO$_2$R$_1$,
  c. AR$_1$, d. R together with $R_o$ and the C to which it is attached form

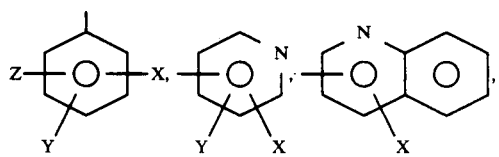

e. R together with $R_o$ and the C to which it is attached form

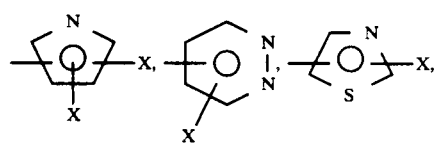

$p_1$ and $p_2$ are independently 0 or 1; provided that $p_2$, and $p_2$ are not both O;

$R_1$ is
a. H,
b. aryl, or a heteroaryl group of 5 to 10 atoms, including one to two heteroatoms, selected from:

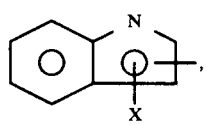

c. phenyl $S(O)_n$-wherein n is 0 to 2,
d. $C_{3-6}$ cycloalkyl;

M is O, N or S;

A is
a.

$\overset{R_2}{\underset{|}{CH}}$, b.

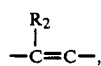

$-\overset{R_2}{\underset{|}{C}}=C-$, c. NH;

$R_2$ is
a. H,
b. $C_{1-5}$ alkoxy,
c. $C_{1-5}$ alkyl,
d. OH,
e. $OC(O)CH_3$;

W is
a. $C_{1-5}$ alkyl,
b. $C_{1-5}$ alkoxy,
c. $NO_2$,
d. $NHR_3$,
e. halogen,
f. $COOR_3$,
g. $OCOR_3$,
h. $NHCOR_3$,
i. $NHSO_2R_3$,
j. $NHSO_2$phenyl;

X, Y, and Z are independently selected from:
a. H,
b. halogen,
c. $C_{1-5}$ alkyl
d. Chd $1$-$5$ alkoxy,
e. $C_{1-5}$ alkoxycarbonyl
f. $C_{1-5}$ alkylcarbonylamino,
g. amino,
h. phenoxy,
i. phenyl $C_{1-5}$ alkoxy,
j. $C_{1-5}$ alkyl$SO_2NH$,
k. $NO_2$,
l. diphenylmethyloxycarbonyl,
m. $C_{1-5}$ alkylthio,
n. aminocarbonyl,
o. carboxy.
p. $C_{2-5}$alkenyloxy
q. $C_{1-5}$alkylamido,
r. trifluoromethyl.

2. A compound of claim 1 wherein:
R is $O-(CO)p_2-(A)p_1-R_1$ or $OSO_2R_1$ and $R_o$ and $R_5$ are H.

3. A compound of claim 2 wherein:
R is $O-(CO)p_2-(A)p_1 R_1$.

4. A compound of claim 3 wherein $p_1$ is 0 and $p_2$ is 1 and Q is 4-methylphenyl.

5. A compound of claim 4 selected from the group wherein:

| | $R_3$ | $R_4$ | and the configuration at the 3,4 position is |
|---|---|---|---|
| a. | $CH_3CH_2$— | 3-thienyl$CO_2CH_2$— | cis |
| b. | $CH_3CH_2$— | 3-methanesulfonamidophenyl-$Co_2CH_2$— | cis |
| c. | $CH_3CH_2$— | 2-nitrophenyl$CO_2CH_2$— | cis |
| d. | $CH_3CH_2$— | 4-pyridyl$CO_2CH_2$— | cis |
| e. | $CH_3CH_2$— | 2-pyridyl$CO_2CH_2$— | cis |
| f. | $CH_3CH_2$— | 5-(2-methoxypyridyl)$CO_2CH_2$— | cis |
| g. | $CH_3CH_2$— | 2-furanyl$CO_2CH_2$— | cis |
| h. | $CH_3CH_2$— | 2-(5-n-butylpyridyl)$CO_2CH_2$— | cis |
| i. | $CH_3CH_2$— | 4-methoxyphenyl$CO_2CH_2$— | cis |
| j. | $CH_3CH_2$— | 4-methoxyphenyl$CO_2CH_2$— | cis |
| k. | $CH_3CH_2$— | 3-nitrophenyl$CO_2CH_2$— | 3S,4S |
| l. | $CH_3CH_2$— | 2-$CH_3SO_2NH$phenyl$CO_2CH_2$— | 3R,4R |

-continued

| | $R_3$ | $R_4$ | and the configuration at the 3,4 position is |
|---|---|---|---|
| m. | $CH_3CH_2$— | 4-pyridazinyl$CO_2CH_2$— | cis |
| n. | $CH_3CH_2$— | 2-$NH_2$phenyl$CO_2CH_2$— | cis |
| o. | $CH_3CH_2$— | 3-furanyl$CO_2CH_2$— | cis |
| p. | $CH_3CH_2$— | 2-quinolinyl$CO_2CH_2$— | cis |
| q. | $CH_3CH_2$— | 4-benzyloxyphenyl$Co_2CH_2$— | cis |
| r. | $CH_3CH_2$— | 4-quinolinyl$CO_2CH_2$— | cis |
| s. | $CH_3CH_2$— | 2-thienyl$CO_2CH_2$— | cis |
| t. | $CH_3CH_2$— | 3-(2-phenoxypyridyl)$CO_2CH_2$— | cis |
| u. | $CH_3CH_2$— | 3-$CH_3CONH$phenyl$CO_2CH_2$— | cis |
| v. | $CH_3CH_2$— | 3-$NH_2$phenyl$CO_2CH_2$— | cis |
| w. | $CH_3CH_2$— | 4-$((Ph)_2COOC)$phenyl$CO_2CH_2$— | cis |
| x. | $CH_3CH_2$— | 4-HOOCphenyl$CO_2CH_2$— | cis |
| y. | $CH_3CH_2$— | 4-$NO_2$phenyl$CO_2CH_2$— | cis |
| z. | $CH_3CH_2CH_2$— | 4-$CH_3O$phenyl$CO_2CH_2$— | cis |
| aa. | $HOCH_2$— | 4-$CH_3O$phenyl$CO_2CH_2$— | cis |
| bb. | $CH_3CH_2$— | 3-pyridyl$CO_2CH_2$— | cis |
| cc. | $CH_3CH_2$— | 4-$CH_3O$phenyl$CO_2CH_2$— | cis |
| dd. | $CH_3CH_2$— | phenyl$CO_2CH_2$— | cis |
| ee. | $CH_3CH_2$— | 3-Coumaryl$CO_2CH_2$— | cis |
| ff. | $CH_3CH_2$— | 2-benzofuranyl$CO_2CH_2$— | cis |
| gg. | $CH_3CH_2$— | 2-furanyl$CO_2CH_2$— | S,S |
| hh. | $CH_3CHCH_3$— | 4-methoxyphenyl$CO_2CH_2$— | cis |
| ii. | $CH_3CH_2$— | 4-$CH_3O_2C$phenyl$CO_2CH_2$— | cis |
| jj. | $CH_3CH_2$— | 4-n-butylcarbamoylphenyl$CO_2CH_2$— | cis |
| kk. | $CH_3CH_2$— | 4-aminophenyl$CO_2CH_2$— | cis |
| ll. | $CH_3CH_2$— | 3-methoxy-4-allyloxy-5-nitrophenyl$CO_2CH_2$— | cis |
| mm. | $CH_3CH_2$— | 3-methoxy-4-allyloxy-5-(methylamido)phenyl$CO_2CH_2$— | cis |
| nn. | $CH_3CH_2$— | 4-methanesulfonamidophenyl$CO_2CH_2$— | cis |
| oo. | $CH_3CH_2$— | 5-(2,3-dimethoxypyridyl)$CO_2CH_2$— | cis |
| pp. | $CH_3CH_2$— | 6-(2,3-dimethoxypyridyl)$CO_2CH_2$— | cis |
| qq. | $CH_3CH_2$— | 4-(2-methoxythiazoly)$CO_2CH_2$— | cis |
| rr. | $CH_3CH_2CH_2$— | 4-$CH_3O$phenyl$CO_2CH_2$— | trans |
| ss. | $HOCH_2$— | 4-$CH_3O$phenyl$CO_2CH_2$— | trans |
| tt. | $CH_3CH_2$— | 4-$CH_3O$phenyl$CO_2CH_2$— | trans |

6. A compound of claim 3 wherein $P_1$ is 1 and $P_2$ is 1.

7. A compound of claim 6 selected from the group wherein:

| | $R_3$ | $R_4$ | and the configuration at the 3,4 position is |
|---|---|---|---|
| a. | $CH_3CH_2$— | 4-$CH_3O$phenylC=$CCO_2CH_2$— | cis |
| b. | $CH_3CH_2$— | 4-$CH_3O$phenyl$CH_2CO_2CH_2$— | cis |
| c. | $CH_3CH_2$— | 3-pyridyl$CH_2CO_2CH_2$— | cis |
| d. | $CH_3CH_2$— | phenyl-(R)-CHO$CH_3CO_2CH_2$— | S,S |
| e. | H | phenyl-(S)-CHO$CH_3CO_2CH_2$— | 4S |
| f. | H | phenyl-(R)-CHO$CH_3CO_2CH_2$— | 4S |
| g. | $CH_3CH_2$— | phenyl-(R)-CHO$CH_3CO_2CH_2$— | cis |
| h. | $CH_3CH_2$— | 3-pyridylC=$CCO_2CH_2$— | cis |
| i. | $CH_3CH_2$— | 3-pyridyl$CH_2CO_2CH_2$— | 3S,4S |
| j. | $CH_3CH_2$— | 4-methoxyphenyl$CH_2CO_2CH_2$— | 3S,4S |
| k. | $CH_3CH_2$— | 4-methoxyphenylC=$CCO_2CH_2$— | 3S,4S |
| l. | $CH_3CH_2$— | 2-furanyl$CH_2CO_2CH_2$— | cis |
| m. | $CH_3CH_2$— | 2-furanylC=$CCO_2CH_2$— | cis |
| n. | $CH_3CH_2$— | phenoxy$CH_2CO_2CH_2$— | cis |
| o. | $CH_3CH_2$— | 3-methyl-4-ethoxyphenyl$CH_2CO_2CH_2$— | cis |
| p. | $CH_3CH_2$— | 2-pyridyl$CH_2CO_2CH_2$— | cis |
| q. | $CH_3CH_2$— | phenylthio$CH_2CO_2CH_2$— | cis |
| r. | $CH_3CH_2$— | 4-ethoxyphenyl$CH_2CO_2CH_2$— | cis |
| s. | $CH_3CH_2$— | 3,4,5-trimethoxyphenyl$CH_2CO_2CH_2$— | cis |
| t. | $CH_3CH_2$— | 3,4,5-trimethoxyphenylC=$CCO_2CH_2$— | cis |
| u. | $CH_3CH_2$— | 3-bromo-4-propanoxy-5-methoyoxyphenylC=$CCO_2CH_2$— | cis |
| v. | $CH_3CH_2$— | 4-methylphenylamino$CO_2CH_2$— | cis |
| w. | $CH_3CH_2$— | cyclohexylamino$CO_2CH_2$— | cis |

-continued

| | $R_3$ | $R_4$ | and the configuration at the 3,4 position is |
|---|---|---|---|
| x. | $CH_3CH_2-$ | 4-trifluoromethylphenylamino$CO_2CH_2-$ | cis |
| y. | $CH_3CH_2-$ | 3,4-dimethoxyphenyl$CH_2CH_2CH_2-$ | cis |
| z. | $CH_3CH_2-$ | 6-(2,3-dimethoxypyridyl)C≡$CCO_2CH_2-$ | cis |
| aa. | $CH_3CH_2-$ | 4-fluorophenylamino$CO_2CH_2-$ | cis. |

8. A compound of claim 2 wherein: R is $OSO_2R_1$.
9. A compound of claim 8 selected from the group wherein:

| $R_3$ is | $R_4$ is | and the configuration at the 3,4 position is |
|---|---|---|
| a. $CH_3CH_2-$ | 4-$CH_3$phenyl$SO_2OCH_2-$ | cis. |

10. A compound of claim 1 wherein:
R is O-(CO)$p_2$-(A)$p_1$-$R_1$, A$R_1$ or R together with $R_o$ and the C to which it s attached form

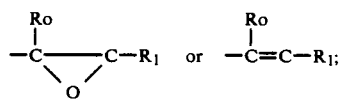

$P_1$ and $P_2$ are independently 0 or 1, provided that $P_1$ and $P_2$ are not both zero;
$R_o$ is H, $CH_3$ or phenyl; provided that when R is O-(CO)$p_2$-(A)$p_1$-$R_1$, $R_o$ is $CH_3$ or phenyl;
$R_5$ is H.
11. A compound of claim 10 wherein:
R is

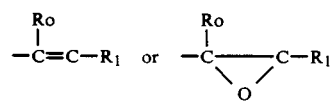

$R_o$ is H, or $CH_3$.
12. A compound of claim 11 selected from the group wherein:

| | $R_3$ is | $R_4$ is | and the configuration at the 3,4 position is |
|---|---|---|---|
| a. | $CH_3CH_2CH_2-$ | phenylC≡C— | trans |
| b. | $CH_3CH_2CH_2-$ | phenylC≡C— | cis |
| c. | $CH_3CH_2-$ | phenylC≡C— | trans |
| d. | $HOCH_2-$ | phenylC≡C— | cis |
| e. | $CH_3CH_2-$ | phenylC≡$CCH_3$ | trans |
| f. | $CH_3CH_2-$ | phenylC≡$CCH_3$ | cis. |

13. A compound of claim 10 wherein:
R is O-(CO)$p_2$-(A)$p_1$-$R_1$ or A$R_1$;
$R_o$ is H, $CH_3$ or phenyl; provided that when R is O-(CO)$p_2$-(A)$p_1$-$R_1$, $R_o$ is $CH_3$ or phenyl.
14. A compound of claim 13 wherein:
$P_1$ is 0.
15. A compound of claim 14 selected from the group wherein:

| | $R_3$ is | $R_4$ is | and the configuration at the 3,4 position is |
|---|---|---|---|
| a. | $CH_3CH_2-$ | 4-$HO_2C$phenylNHCH$_2$— | cis |
| b. | $CH_3CH_2-$ | phenyl$CH_2CH_2-$ | cis |
| c. | $CH_3CH_2-$ | 4-$CH_3O$phenyl$CO_2$CHCH$_3$ | cis |
| d. | $CH_3CH_2-$ | phenyl$CH_2$CHCH$_3$ | cis |
| e. | $CH_3CH_2-$ | 4-$CH_3O$phenyl$CO_2$CHphenyl | cis |
| f. | H | phenylCHCHCH$_3$ / OCOCH$_3$ | |
| g. | H | $CH_3CO_2CH_2$CHCH$_3$. | |

16. A compound of claim 1 wherein;
$R_o$ is H, $CH_3$ or $CH_2$phenyl;
$R_5$ is $C_{1-5}$ alkyl or $C_{1-5}$ alkoxy;
R is O-(CO)$p_2$-(A)$p_1$-$R_1$, A$R_1$ or R together with $R_o$ and the C to which it is attached form

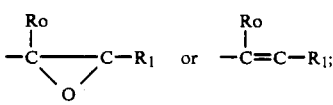

$P_1$ and $P_2$ are independently 0 or 1; provided that $P_1$ and $P_2$ are not both zero.
17. A compound of claim 16 selected from the group wherein:

| | $R_3$ is | $R_5$ is | $R_4$ is |
|---|---|---|---|
| a. | $CH_3$ | $CH_3$ | phenyl$CH_2CH_2-$ |
| b. | $CH_3$ | $CH_3$ | phenyl$CO_2$CHCH$_2$phenyl |
| c. | $CH_3$ | $CH_3$ | phenylCH=CH— |
| d. | $CH_3$ | $CH_3$ | phenylCH—CH—. \O/ |

18. A hypocholesterolemic, hypolipidemic pharmaceutical composition comprising a pharmaceutically acceptable carrier and a therapeutically effective amount of a compound as defined in claim 1.
19. A method of treating hypercholestermia comprising the administration to a sibJect in need of such treatment a therapeutically effective amount of a compound of claim 1.

* * * * *